United States Patent [19]
Allen et al.

[11] Patent Number: 5,407,648
[45] Date of Patent: Apr. 18, 1995

[54] COMBINATION STERILIZATION TRAY AND MAT

[75] Inventors: Kraig H. Allen; Thomas J. Bussell, both of Warsaw, Ind.

[73] Assignee: Paragon Group of Plastics Companies, Inc., Warsaw, Ind.

[21] Appl. No.: 128,806

[22] Filed: Sep. 29, 1993

[51] Int. Cl.6 .................................................. A61L 2/00
[52] U.S. Cl. ................................. 422/297; 206/438; 206/563; 422/292; 422/300
[58] Field of Search .............. 422/292, 297, 300, 310, 422/438; 206/439, 63.5, 563

[56] References Cited

U.S. PATENT DOCUMENTS

| | | | |
|---|---|---|---|
| 2,604,377 | 7/1952 | Eames | 422/300 X |
| 4,617,178 | 10/1986 | Nichols | 422/310 |
| 4,617,943 | 6/1987 | Wahlquist | 422/300 |
| 4,798,292 | 1/1989 | Hauze | 206/439 |
| 4,959,199 | 9/1990 | Brewer | 422/300 |
| 5,098,676 | 3/1992 | Brooks, Jr. | 422/292 |
| 5,165,539 | 11/1992 | Weber et al. | 206/439 X |
| 5,211,915 | 5/1993 | Mönch | 422/102 |

Primary Examiner—Robert J. Warden
Assistant Examiner—Krisanne M. Thornton
Attorney, Agent, or Firm—James D. Hall

[57] ABSTRACT

An sterilization tray and mat used in combination for the sterilization of surgical instruments. The tray includes raised ribs protruding from the tray floor for supporting a sterilization mat above the tray floor and a plurality of holes for permitting the ingress and egress of sterilants and for permitting drainage of condensation. The mat includes a plurality of raised parallel ribs with rows of projections extending from and between each rib for supporting the instruments.

10 Claims, 4 Drawing Sheets

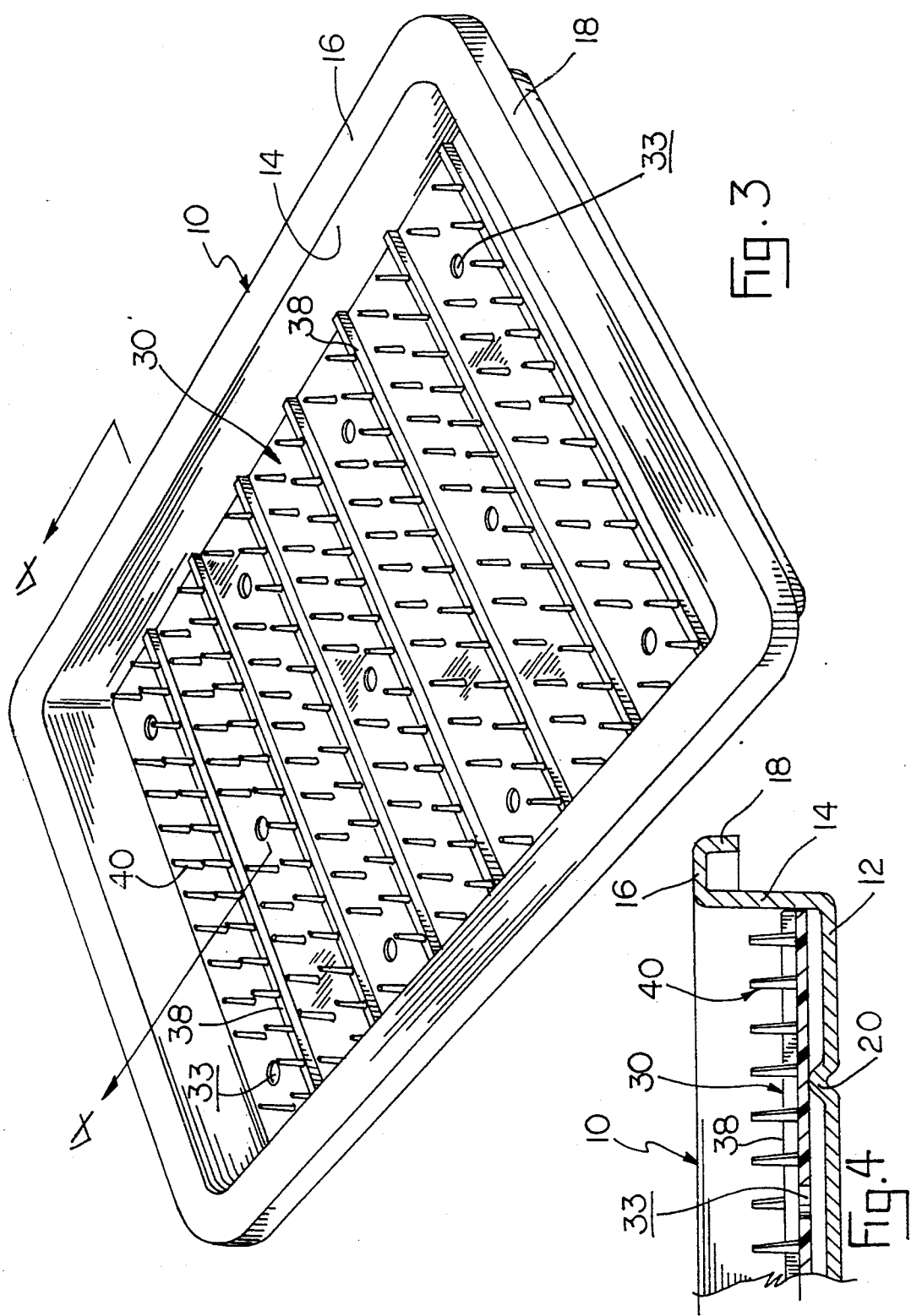

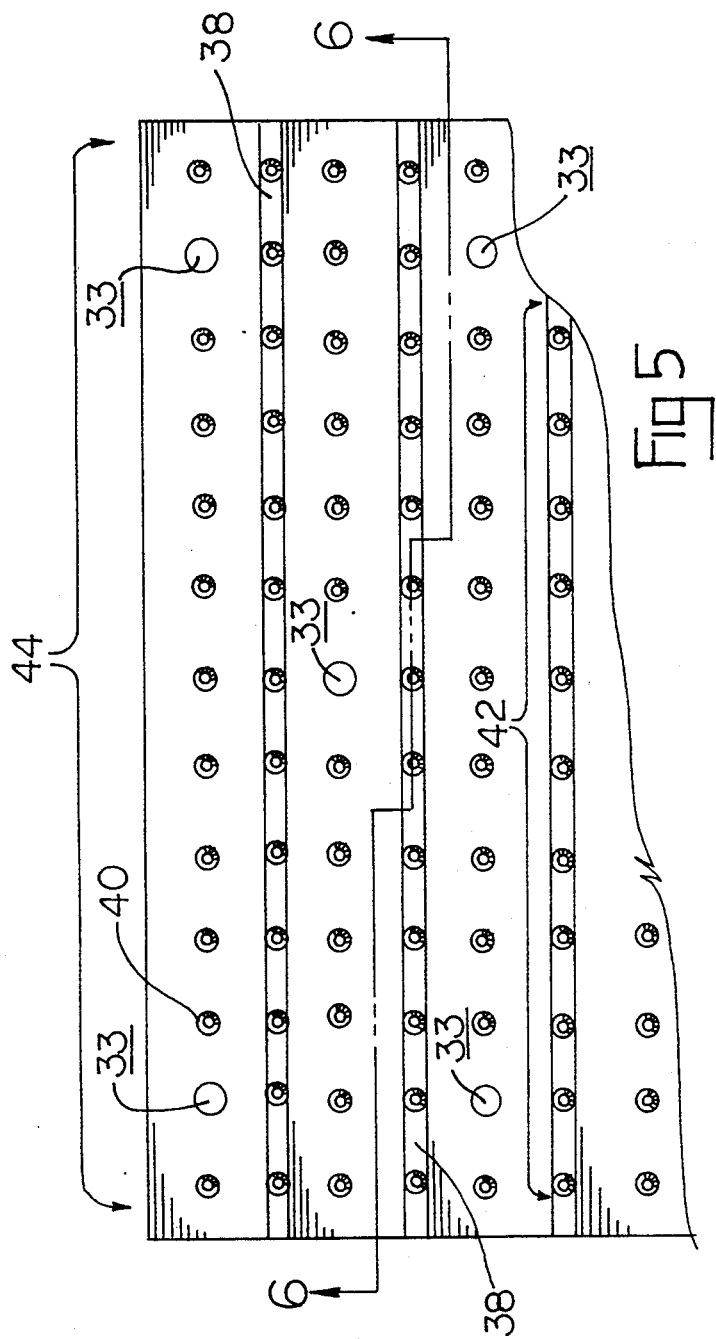
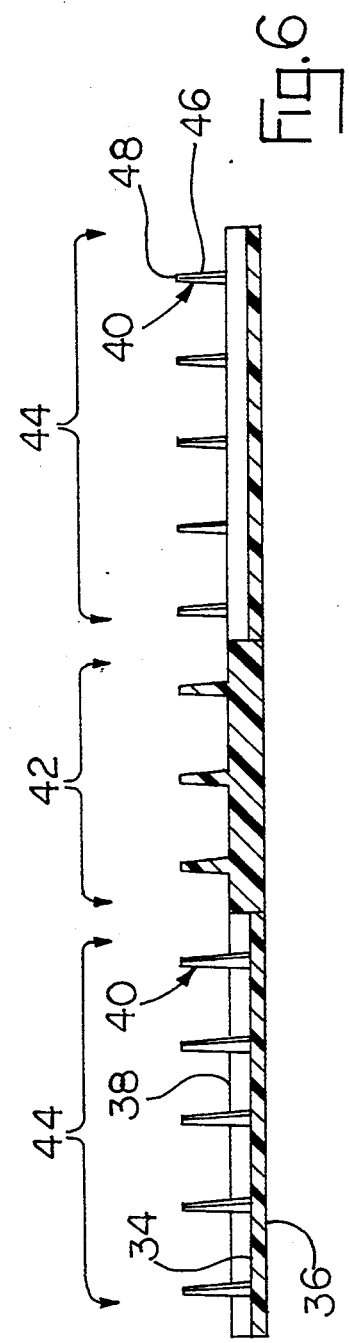

COMBINATION STERILIZATION TRAY AND MAT

FIELD OF THE INVENTION

This invention relates to a combination tray and mat for use in sterilizing, transporting, presenting and storing medical instruments.

BACKGROUND OF THE INVENTION

Conventional sterilization equipment and autoclaves use steam and other sterilants to sterilize medical instruments and other contamination sensitive objects. Generally, the instruments are placed in sterilization trays and the entire tray is placed into the steam bath. The steam and sterilants are introduced through holes in the trays. After the sterilization process, residual steam may collect and condense in the sterilization trays. Unless the condensation is properly drained off, the residue can become a medium for bacteria.

Many sterilization trays use sterilization mats made of silicone or other synthetic materials suitable for sterilization. Often, these mats include raised fingers to support the instruments. Supporting the instruments on the raised fingers reduces the amount of surface contact between the instrument and mat. Reducing surface contact between the instruments and the tray or mat increases the contact of the steam/sterilants with the instruments and minimizes the areas where condensation can collect. For example, U.S. Pat. No. 5,098,676 to John A. Brooks, Jr. discloses the use of sterilization mats including a plurality of raised fingers which extend from the top of the mat and a plurality of feet extending from the bottom of the mat. The fingers support the instruments above the mat and the feet space the mat above the tray floor to promote circulation and drainage of sterilants and to increase the contact of the sterilant with the instruments. During the sterilization process, however, the sterilants heat the sterilization mat, which expands and sags. Consequently, great numbers of feet are required to keep the mat from sagging into contact with the tray floor. Increasing the number of feet impedes the circulation and drainage of the sterilants and increases the area of surface contacts where condensation can adhere and cultivate bacteria, thereby defeating the purpose of the elevated mat. In addition, the raised fingers present other practical problems. Small diameter instruments can fall between the raised fingers to rest against the mat bottom. The raised finger makes retrieving the fallen instrument difficult, especially for users wearing sterile gloves.

SUMMARY OF THE INVENTION

The improved combination sterilization tray and mat of this invention provides several advantages over conventional sterilization trays and mats. The sterilization tray includes raised ribs protruding from the tray floor to support a flat bottomed sterilization mat. The tray ribs formed in the floor space the mat above the tray floor to promote the circulation and drainage of the sterilants between the mat and tray. Consequently, thinner sterilization mats without feet can be used while producing the desired spacing with minimal surface contact between the tray floor and the mat. The tray ribs also eliminate the need for the drainage holes in the tray and mat to be aligned.

The sterilization mat of this invention includes a plurality of raised ribs extending from its top surface. A plurality of vertically protruding fingers extends from the mat's top surface which are aligned in parallel rows. A row of fingers is located between each rib while a row of shorter fingers also extends along the tops of each rib. The tips of the fingers provide an even surface upon which the instruments are placed. The raised mat ribs are positioned perpendicularly to the tray ribs to provide additional support. The mat ribs also prevent small diameter instruments which may fall between the fingers from resting against the mat floor. The mat ribs allow the fallen instruments to be retrieved easily as well as improve the sterilant circulation and drainage about the fallen instruments.

Accordingly, an object of this invention is to provide for a novel and unique combination of a sterilization tray and mat.

Another object is to provide for a sterilization tray with a plurality of raised ribs for supporting a sterilization mat above the floor of the tray to promote the drainage of condensation and the circulation of sterilants during the sterilization process.

Another object is to provide for a sterilization mat which includes a plurality of raised parallel ribs and a plurality of vertically extending fingers for supporting instruments to be sterilized.

Other objects will become apparent upon a reading of the following description.

BRIEF DESCRIPTION OF THE DRAWINGS

A preferred embodiment of the invention has been depicted for illustrative purposes only wherein:

FIG. 3 is a perspective view of the sterilization tray and mat;

FIG. 4 is a sectional view of the sterilization tray and mat taken along line 4—4 of FIG. 3;

FIG. 5 is a top plan view of the sterilization mat; and

FIG. 6 is a sectional view taken along line 3—3 of FIG. 2.

DESCRIPTION OF THE PREFERRED EMBODIMENT

The preferred embodiment herein described is not intended to be exhaustive or to limit the invention to the precise form disclosed. It is chosen and described to explain the principles of the invention and its application and practical use to enable others skilled in the art to utilize its teachings.

Figure 1:
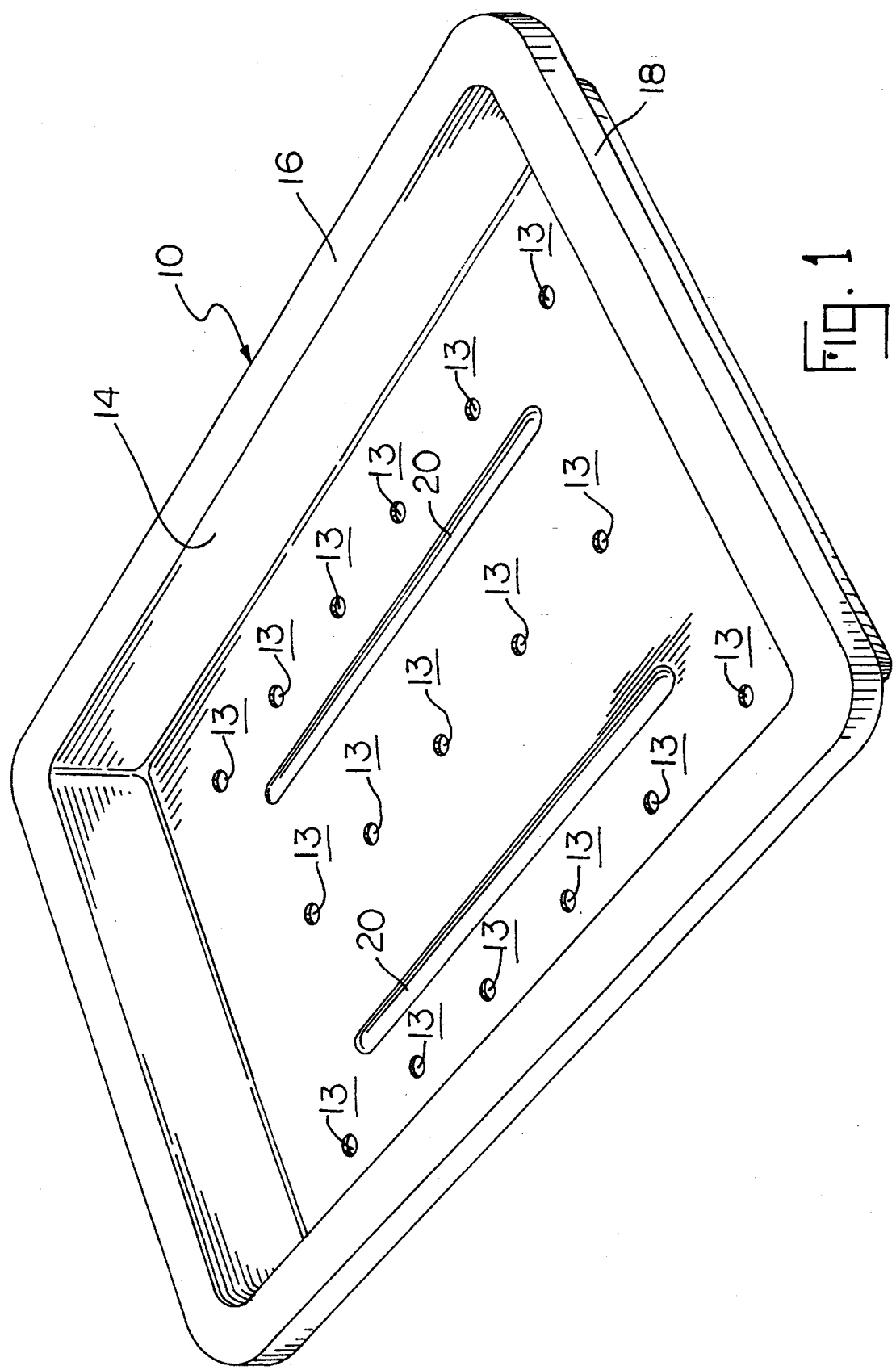
FIG. 1 is a perspective of the sterilization tray of this invention.
Figure 2:
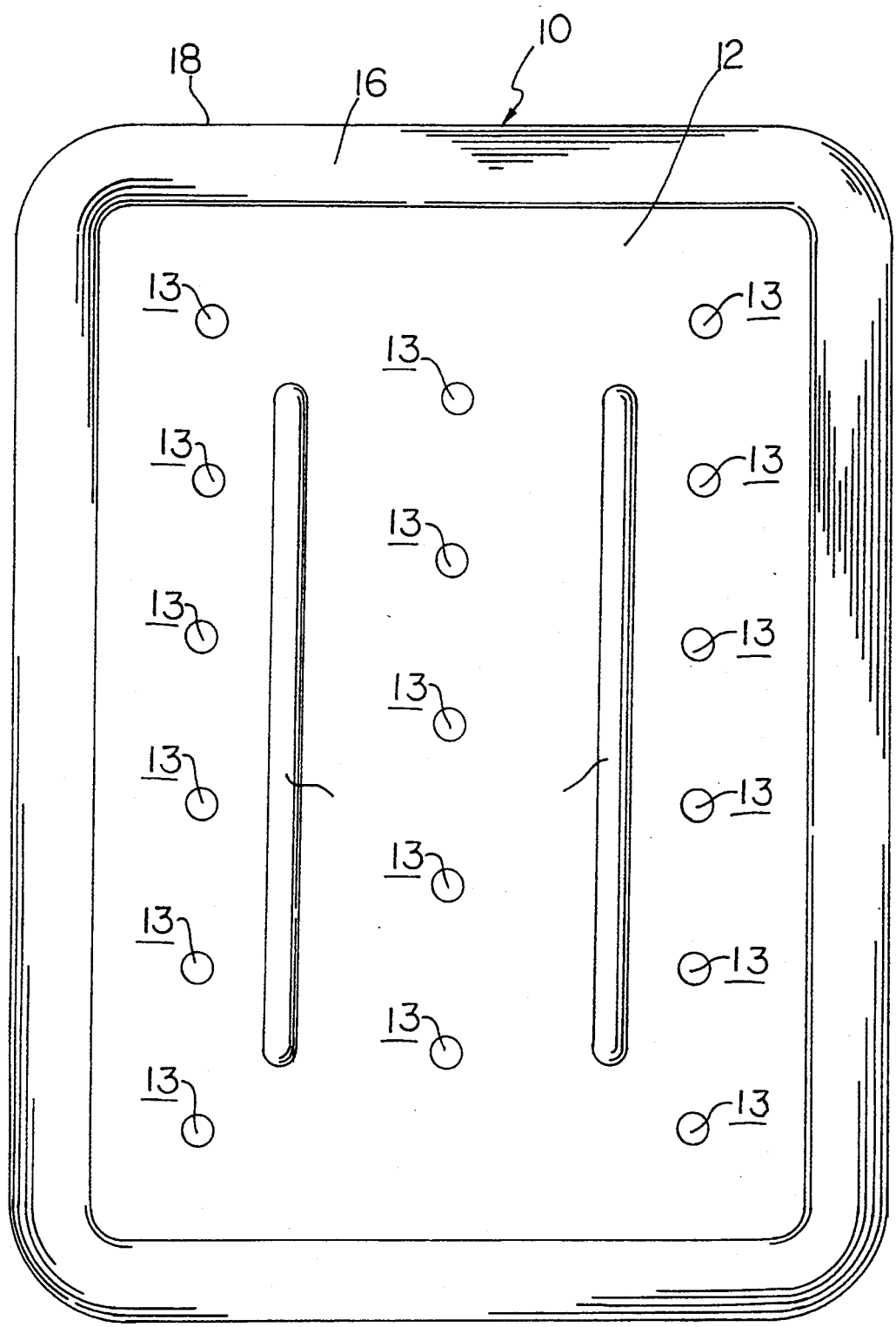
FIG. 2 is a top view of the sterilization tray.

FIGS. 1 and 2 show the sterilization tray 10 of this invention. Tray 10 is used for sterilization, transport and storage of surgical instruments and other contaminant sensitive objects. Sterilization tray 10 is generally constructed of a non-corrosive metal such as aluminum or a suitable composite material such as a thermoplastic resin. Tray 10 can also be constructed in a variety of dimensions and sizes depending on the application. As shown, tray 10 includes a floor 12 with four raised integral side walls 14. Each side wall 14 terminates in an outturned flange 16 and a downturned lip 18. Tray floor 12 has a plurality of holes 13 spaced in a predetermined pattern. Holes 13 allow the ingress and egress of steam and other gaseous sterilants and also provide for the drainage of any condensation. As shown in FIGS. 1 and 2, tray floor 12 also has a pair of raised parallel ribs 20. Tray ribs 20 are formed by indentations formed in the under surface of tray floor 12. Tray ribs 20 provide a support for a sterilization mat 30. Although two tray ribs are shown in the figures, any number of parallel ribs may be used.

As shown in FIGS. 3-6, sterilization mat 30 includes a mat body or floor 32 formed of flexible heat and moisture resistent material such as silicone rubber, plastic or other synthetic or natural material. Mat body 32 has a top surface 34 and bottom surface 36. Top surface 34 includes a plurality of parallel spaced raised ribs 38. Mat body 32 also has a plurality of holes 33 located between mat ribs 38 in a predetermined pattern. A plurality of upwardly protruding fingers 40 extend from the top surface 34 of mat body 32. Each mat rib 38 includes a row 42 of fingers 40. As shown, a row 44 of fingers 40 also extends from side-to-side across mat surface 34 between adjacent mat ribs 38. Each finger 40 is defined by a generally conical side wall 46, which terminates in a substantially flat upper tip 48. The fingers extending from rows 44 are slightly longer than the fingers in rows 42 to produce a flat and even elevated platform for supporting surgical instruments (not shown).

FIGS. 3 and 4 show tray 10 in combination with mat 30. Mat 30 is sized to fit tray 10 and rests atop raised tray ribs 20. Tray ribs 20 space mat 30 away from tray floor 12. Preferably, mat 30 is positioned in tray 10 with mat ribs 38 running perpendicularly to tray ribs 20. Mat ribs 38 provide additional support to mat 30. Elevating the sterilization mat 30 above the tray floor 12 on tray ribs 20 promotes the circulation and drainage of sterilants between tray floor 12 and bottom surface 36 of mat 30. Mat ribs 38 and fingers 40 also promote the circulation and drainage of sterilants by increasing the contact of the steam/sterilants with the instruments and minimizing the areas where condensation can collect and incubate bacteria. In addition, mat ribs 38 prevent small diameter instruments which may fall between fingers 40 from resting against mat top surface 34. With the fallen instruments supported on mat ribs 38, the fallen instruments to be retrieved easily.

It is understood that the above description does not limit the invention to the details given, but may be modified within the scope of the following claims.

I claim:

1. An apparatus for sterilizing and storing medical instruments, comprising:
   a tray having a floor, said floor having a plurality of spaced holes therein and a plurality of spaced ribs extending upwardly from said floor, said holes permitting ingress and egress of sterilants, and drainage of condensation; and
   a flexible sterilization mat for supporting instruments and sized to fit within said tray, said mat being seated on top of said floor and having a lower surface and an upper surface, said lower surface resting on and being supported by said ribs whereby said lower surface is spaced above said floor, and a plurality of raised ribs on said upper surface of said mat for stiffening said mat and for preventing instruments from resting against said upper surface.

2. The apparatus of claim 1, wherein said ribs on the upper surface of the mat extend transversely with respect to the ribs on the floor of the tray.

3. The apparatus of claim 1 wherein said mat has a plurality of holes, said mat holes permitting ingress and egress of sterilants and also permitting drainage of condensation.

4. The apparatus of claim 3 wherein said mat further includes a plurality of upwardly extending fingers, said fingers supporting said instruments, said ribs preventing instruments that fall off of said fingers from resting on said mat upper surface.

5. The apparatus of claim 4, wherein at least some of said fingers extend upwardly from the ribs.

6. The apparatus of claim 4 wherein at least one of said fingers extends upwardly from said mat body between each said rib.

7. A sterilization mat for supporting an instrument to be sterilized and for use in a sterilization tray having a plurality of holes therein, said mat comprising:
   a mat body having an upper body surface and a plurality of holes through said mat,
   a plurality of fingers extending upwardly from said mat body upper surface for supporting instruments, and
   a plurality of upwardly extending raised ribs on said mat body upper surface to stiffen said mat and to prevent instruments from falling between the fingers from resting against said mat body upper surface.

8. The mat of claim 7 wherein each said rib has at least one of said fingers extending upwardly therefrom.

9. The mat of claim 7 wherein said ribs are spaced and oriented in a generally parallel manner.

10. The mat of claim 7 wherein at least one of said fingers extends upwardly from said mat body between two of said ribs.

* * * * *